US011833261B2

(12) United States Patent
Chen et al.

(10) Patent No.: US 11,833,261 B2
(45) Date of Patent: Dec. 5, 2023

(54) LIGHTING APPARATUS

(71) Applicant: LEEDARSON LIGHTING CO.,LTD., Fujian (CN)

(72) Inventors: Ying Chen, Fujian (CN); Xinwen Lin, Fujian (CN); Lina Bai, Fujian (CN); Jinfu Chen, Fujian (CN); Zhenyu Tang, Fujian (CN); Shuxing Gao, Fujian (CN); Xu Wu, Fujian (CN)

(73) Assignee: LEEDARSON LIGHTING CO., LTD., Fujian (CN)

( * ) Notice: Subject to any disclaimer, the term of this patent is extended or adjusted under 35 U.S.C. 154(b) by 44 days.

(21) Appl. No.: 17/563,684

(22) Filed: Dec. 28, 2021

(65) Prior Publication Data

US 2022/0202972 A1    Jun. 30, 2022

(30) Foreign Application Priority Data

Dec. 28, 2020  (CN) .......................... 202023231237.0
Dec. 28, 2020  (CN) .......................... 202023231394.1
Dec. 28, 2020  (CN) .......................... 202023231674.2
Dec. 28, 2020  (CN) .......................... 202023231693.5

(51) Int. Cl.
| | |
|---|---|
| *A61L 2/10* | (2006.01) |
| *F21V 7/24* | (2018.01) |
| *F21V 23/00* | (2015.01) |
| *F21V 7/04* | (2006.01) |
| *A61L 2/24* | (2006.01) |
| *F21V 23/04* | (2006.01) |
| *F21Y 115/10* | (2016.01) |
| *F21Y 113/10* | (2016.01) |

(52) U.S. Cl.
CPC .................. *A61L 2/10* (2013.01); *A61L 2/24* (2013.01); *F21V 7/04* (2013.01); *F21V 7/24* (2018.02); *F21V 23/003* (2013.01); *F21V 23/0471* (2013.01); *A61L 2202/11* (2013.01); *A61L 2202/14* (2013.01); *F21Y 2113/10* (2016.08); *F21Y 2115/10* (2016.08)

(58) Field of Classification Search
CPC ..... A61L 2/10; A61L 2/24; F21V 7/24; F21V 7/04; F21V 23/003; F21V 23/0471
See application file for complete search history.

(56) References Cited

U.S. PATENT DOCUMENTS

| | | | |
|---|---|---|---|
| 9,951,924 B2 * | 4/2018 | Kang | ......................... F21K 9/64 |
| 2004/0105264 A1 * | 6/2004 | Spero | .................. F21V 23/0471 |
| | | | 362/276 |
| 2007/0138978 A1 * | 6/2007 | Rains | ...................... G09F 13/22 |
| | | | 315/291 |

(Continued)

*Primary Examiner* — Bryon T Gyllstrom
(74) *Attorney, Agent, or Firm* — Chun-Ming Shih; LANWAY IPR SERVICES (57) ABSTRACT

A lighting apparatus includes a first light source, a second light source, a first reflective cup, a second reflective cup, a base housing and a driver. The first light source is used for emitting a first light. The second light source is used for emitting a second light. The first reflective cup is used for limiting the first light in a first scope. The second reflective cup is used for limiting the second light in a second scope. The base housing is used for disposing the first reflective cup and the second reflective cup. The driver selectively provides a first driving current to the first light source and a second driving current to the second light source.

18 Claims, 12 Drawing Sheets

(56) References Cited

U.S. PATENT DOCUMENTS

| | | | | |
|---|---|---|---|---|
| 2009/0021931 A1* | 1/2009 | Mayer | ............... | F21V 7/04 |
| | | | | 362/235 |
| 2011/0002115 A1* | 1/2011 | Okamura | ............... | F21V 7/24 |
| | | | | 362/147 |
| 2011/0181167 A1* | 7/2011 | Cho | ............... | F21V 7/04 |
| | | | | 313/46 |
| 2012/0236559 A1* | 9/2012 | Sachsenweger | ............... | F21V 7/04 |
| | | | | 362/235 |
| 2013/0306998 A1* | 11/2013 | Ulasyuk | ............... | C09K 11/7774 |
| | | | | 257/88 |
| 2017/0114980 A1* | 4/2017 | Madril | ............... | F21V 7/24 |
| 2019/0376653 A1* | 12/2019 | Dussaume | ............... | F21K 9/69 |

\* cited by examiner

LIGHTING APPARATUS

FIELD

The present invention is related to a lighting apparatus, and more particularly related to a lighting apparatus with two types of light sources.

BACKGROUND

The time when the darkness is being lighten up by the light, human have noticed the need of lighting up this planet. Light has become one of the necessities we live with through the day and the night. During the darkness after sunset, there is no natural light, and human have been finding ways to light up the darkness with artificial light. From a torch, candles to the light we have nowadays, the use of light have been changed through decades and the development of lighting continues on.

Early human found the control of fire which is a turning point of the human history. Fire provides light to bright up the darkness that have allowed human activities to continue into the darker and colder hour of the hour after sunset. Fire gives human beings the first form of light and heat to cook food, make tools, have heat to live through cold winter and lighting to see in the dark.

Lighting is now not to be limited just for providing the light we need, but it is also for setting up the mood and atmosphere being created for an area. Proper lighting for an area needs a good combination of daylight conditions and artificial lights. There are many ways to improve lighting in a better cost and energy saving. LED lighting, a solid-state lamp that uses light-emitting diodes as the source of light, is a solution when it comes to energy-efficient lighting. LED lighting provides lower cost, energy saving and longer life span.

The major use of the light emitting diodes is for illumination. The light emitting diodes is recently used in light bulb, light strip or light tube for a longer lifetime and a lower energy consumption of the light. The light emitting diodes shows a new type of illumination which brings more convenience to our lives. Nowadays, light emitting diode light may be often seen in the market with various forms and affordable prices.

After the invention of LEDs, the neon indicator and incandescent lamps are gradually replaced. However, the cost of initial commercial LEDs was extremely high, making them rare to be applied for practical use. Also, LEDs only illuminated red light at early stage. The brightness of the light only could be used as indicator for it was too dark to illuminate an area. Unlike modern LEDs which are bound in transparent plastic cases, LEDs in early stage were packed in metal cases.

In 1878, Thomas Edison tried to make a usable light bulb after experimenting different materials. In November 1879, Edison filed a patent for an electric lamp with a carbon filament and keep testing to find the perfect filament for his light bulb. The highest melting point of any chemical element, tungsten, was known by Edison to be an excellent material for light bulb filaments, but the machinery needed to produce super-fine tungsten wire was not available in the late 19th century. Tungsten is still the primary material used in incandescent bulb filaments today.

Early candles were made in China in about 200 BC from whale fat and rice paper wick. They were made from other materials through time, like tallow, spermaceti, colza oil and beeswax until the discovery of paraffin wax which made production of candles cheap and affordable to everyone. Wick was also improved over time that made from paper, cotton, hemp and flax with different times and ways of burning. Although not a major light source now, candles are still here as decorative items and a light source in emergency situations. They are used for celebrations such as birthdays, religious rituals, for making atmosphere and as a decor.

Illumination has been improved throughout the times. Even now, the lighting device we used today are still being improved. From the illumination of the sun to the time when human can control fire for providing illumination which changed human history, we have been improving the lighting source for a better efficiency and sense. From the invention of candle, gas lamp, electric carbon arc lamp, kerosene lamp, light bulb, fluorescent lamp to LED lamp, the improvement of illumination shows the necessity of light in human lives.

There are various types of lighting apparatuses. When cost and light efficiency of LED have shown great effect compared with traditional lighting devices, people look for even better light output. It is important to recognize factors that can bring more satisfaction and light quality and flexibility.

It is important to add features to light devices. When LED technologies develop, more and more functions are expected to be added.

Sterilization is one of the functions expected, particularly when virus is broadcasted around the world in recent years. However, it is important to prevent damages to human body when such function is added.

Furthermore, it is also important to provide a compact design that has low cost while providing certain flexibility. It is important to add features to light devices. When LED technologies develop, more and more functions are expected to be added.

SUMMARY

In some embodiments, a lighting apparatus includes a first light source, a second light source, a first reflective cup, a second reflective cup, a base housing and a driver.

The first light source is used for emitting a first light.

The second light source is used for emitting a second light.

The first reflective cup is used for limiting the first light in a first scope.

The second reflective cup is used for limiting the second light in a second scope.

The base housing is used for disposing the first reflective cup and the second reflective cup.

The driver selectively provides a first driving current to the first light source and a second driving current to the second light source.

In some embodiments, the first light is a ultra-violet light.

In some embodiments, the first reflective cup is surrounded by the second reflective cup.

In some embodiments, the second light source includes multiple second LED modules.

The first light source and the multiple second LED modules are disposed on a same circuit board.

The multiple second LED modules surround the first light source.

In some embodiments, the first reflective cup includes aluminum material.

In some embodiments, the second reflective cup is made of plastic material.

In some embodiments, the lighting apparatus may also include a first light passing cover and a second light passing cover.

The first second light passing cover has a cover opening for fixing the first light passing cover.

The first light passes through the first light passing cover.

The second light passes through the second light passing cover.

In some embodiments, first light passing cover is made of silica glass material.

In some embodiments, the lighting apparatus may also include a motion sensor.

The driver turns off the first driving current when the motion sensor indicates an object approaching the first scope.

In some embodiments, the base housing includes a surface rim for concealing a cavity for installing the lighting apparatus.

The surface rim has a sensor hole for the motion sensor to detect the object.

In some embodiments, the motion sensor is integrated with the driver.

The motion sensor is placed to a motion detection groove of the surface rim for facing to the sensor hole.

In some embodiments, the lighting apparatus may also include a wireless sensor for receiving an external command from a remote control.

In some embodiments, the wireless sensor is integrated with the motion sensor and placed facing to the sensor hole.

In some embodiments, the base housing is a downlight housing with a pair of elastic units to attach to a cavity.

In some embodiments, the first reflective cup is moved by a motor for changing a direction of the first light to scan a sterilization zone.

In some embodiments, the driver is electrically connected to a wall switch mounted on a wall.

The driver detects a predetermined on-off pattern of an operation to the wall switch to determine activating the first light source to perform sterilization.

In some embodiments, the driver waits a waiting time period before turning on the first light source after the predetermined on-off pattern being detected.

In some embodiments, when the sterilization is performed, the second light emits by the second light source is changed to a different light parameter.

In some embodiments, the second light source emits a different color of the second light during sterilization.

In some embodiments, the first reflective cup surrounds the first reflective cup.

The first scope is larger than the second scope.

DETAILED DESCRIPTION

Figure 12:
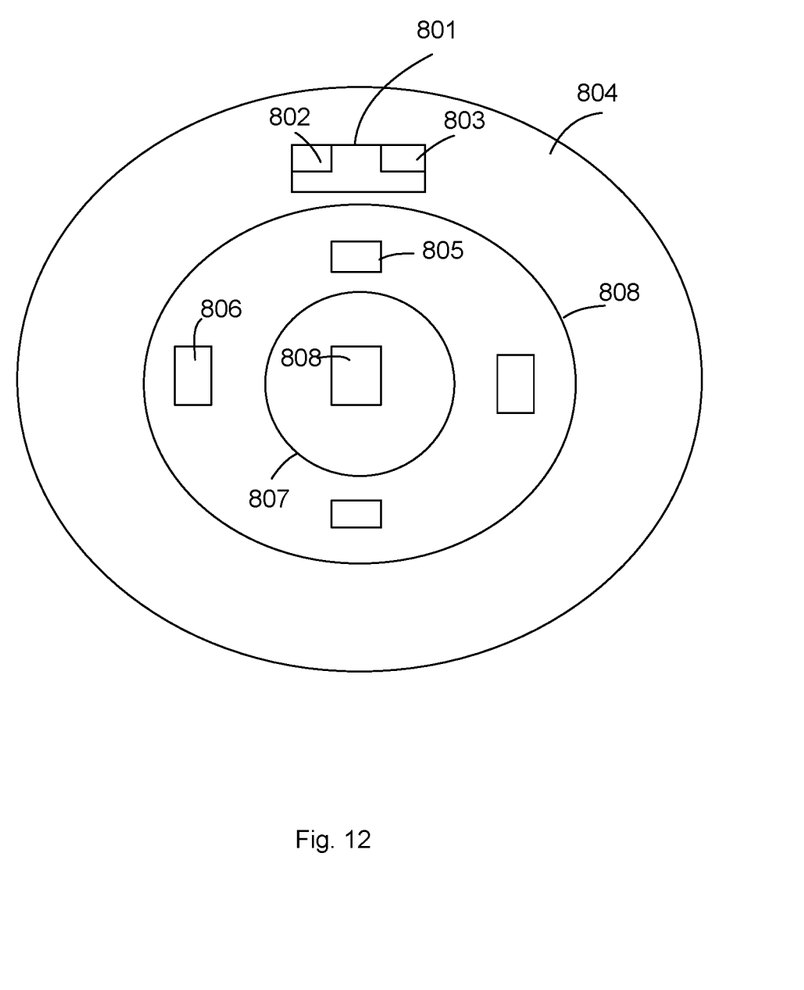
FIG. 12 illustrates a bottom view of another lighting apparatus embodiment.
Figure 13:
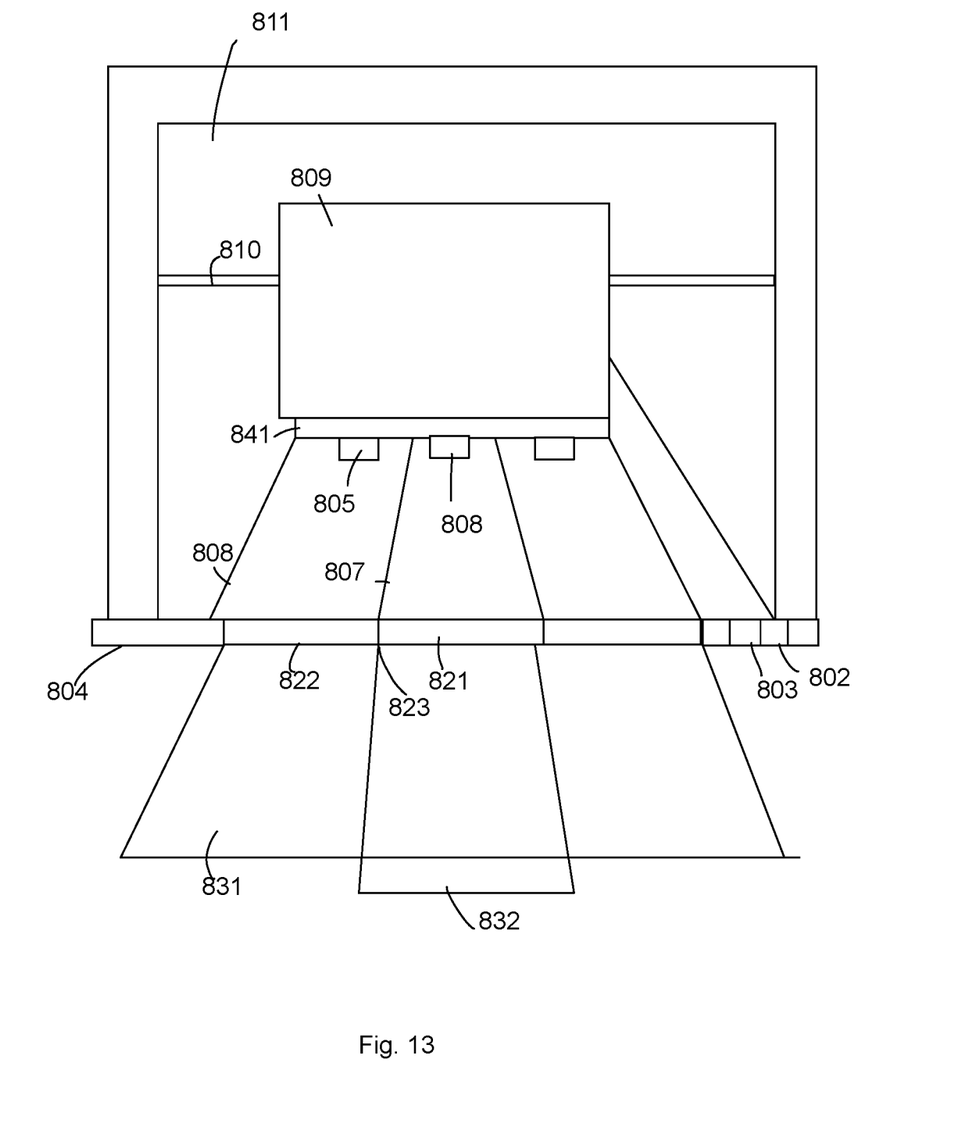
FIG. 13 illustrates a side view of the example in FIG. 12.

Please refer to FIG. 12 and FIG. 13. FIG. 12 illustrates a bottom view of a lighting apparatus embodiment and FIG. 13 illustrates a side view of the example in FIG. 12.

In FIG. 12 and FIG. 13, a lighting apparatus includes a first light source 808, a second light source 805, a first reflective cup 807, a second reflective cup 808, a base housing 841 and a driver 809. The base housing 841 has a surface rim 804 for concealing a cavity 811 in a ceiling for installing the lighting apparatus. There are a pair of elastic units 810 for keeping the lighting apparatus to stay in the cavity 811.

The first light source 808 is used for emitting a first light, e.g. an ultra-violet light that can be used for performing sterilization.

Ultraviolet germicidal irradiation (UVGI) is a disinfection method that uses short-wavelength ultraviolet (ultraviolet C or UV-C) light to kill or inactivate microorganisms by destroying nucleic acids and disrupting their DNA, leaving them unable to perform vital cellular functions. UVGI is used in a variety of applications, such as food, air, and water purification.

UV-C light is weak at the Earth's surface since the ozone layer of the atmosphere blocks it. UVGI devices can produce strong enough UV-C light in circulating air or water systems to make them inhospitable environments to microorganisms such as bacteria, viruses, molds, and other pathogens. UVGI can be coupled with a filtration system to sanitize air and water.

The application of UVGI to disinfection has been an accepted practice since the mid-20th century. It has been used primarily in medical sanitation and sterile work facilities. Increasingly, it has been employed to sterilize drinking and wastewater since the holding facilities are enclosed and can be circulated to ensure a higher exposure to the UV. UVGI has found renewed application in air purifiers.

The second light source 805 is used for emitting a second light.

The first reflective cup 807 is used for limiting the first light in a first scope 832.

The second reflective cup 808 is used for limiting the second light in a second scope 831.

The base housing 841 is used for disposing the first reflective cup 807 and the second reflective cup 808.

In this example, the second light source 805 has multiple LED modules 806 surrounding the first light source 808. In addition, the first reflective cup 808 is surrounded by the second reflective cup 808.

The driver 809 selectively provides a first driving current to the first light source 808 and a second driving current to the second light source 805.

The first light source 808 and the second light source 805 may include multiple types of LED modules so that the driver 809 may control and adjust the driving currents to different types of LED modules to change a light parameter, e.g. a mixed color or a mixed color temperature.

In some embodiments, the first light is a ultra-violet light.

In some embodiments, the first reflective cup is surrounded by the second reflective cup.

In some embodiments, the second light source includes multiple second LED modules.

Figure 2:
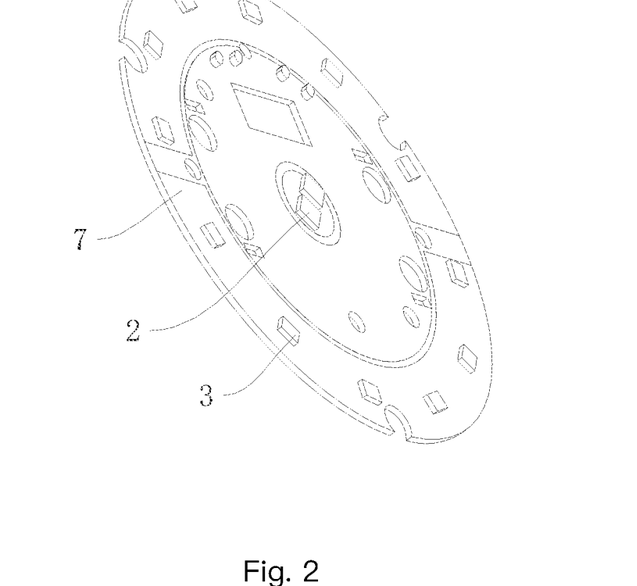
FIG. 2 illustrates an light source plate example.

In FIG. 2, the first light source 2 and the multiple second LED modules 3 are disposed on a same circuit board 7.

The multiple second LED modules 3 surround the first light source 2.

In some embodiments, the first reflective cup includes aluminum material.

In some embodiments, the second reflective cup is made of plastic material. This is particularly helpful when the first light is an ultra-violet light while the second light is a normal light.

In FIG. 12 and FIG. 13, the lighting apparatus may also include a first light passing cover 822 and a second light passing cover 821.

The second light passing cover 822 has a cover opening 823 for fixing the first light passing cover 821.

The first light passes through the first light passing cover 821.

The second light passes through the second light passing cover 822.

In some embodiments, first light passing cover is made of silica glass material.

In some embodiments, the lighting apparatus may also include a motion sensor 803.

The driver 809 turns off the first driving current when the motion sensor 803 indicates an object approaching the first scope 832.

In some embodiments, the base housing 841 includes a surface rim 804 for concealing a cavity 811 for installing the lighting apparatus.

The surface rim 804 has a sensor hole 801 for the motion sensor 803 to detect the object. The motion sensor 803 may be an infrared sensor or a microwave sensor. The sensor hole 801 decrease influence for collecting data.

In some embodiments, the motion sensor is integrated with the driver.

Figure 8:
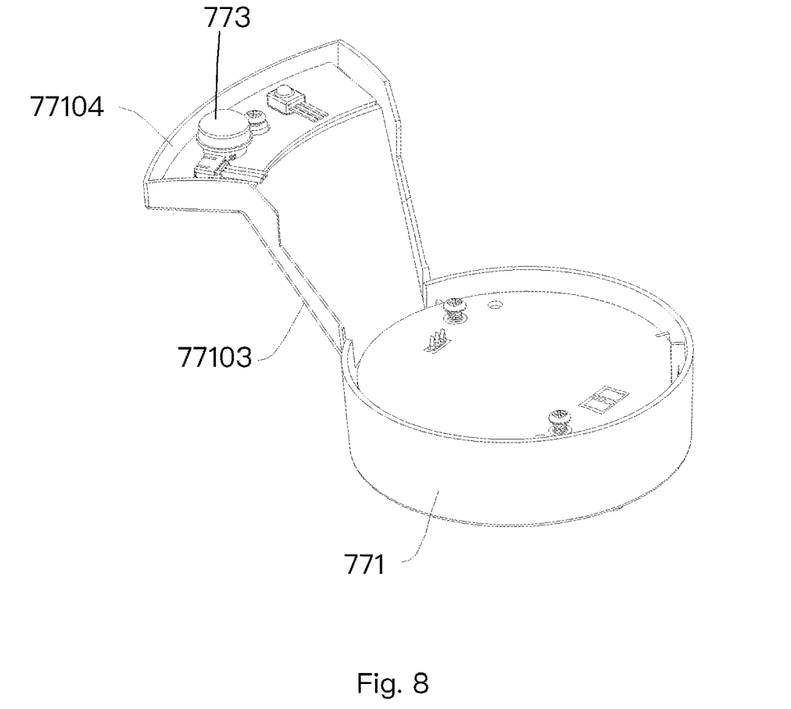
FIG. 8 illustrates a driver with a sensor module.

For example, FIG. 8 shows a driver box 771 with an extending bar 77103 holding a sensor module 77102 that has a motion sensor.

The motion sensor is placed to a motion detection groove of the surface rim for facing to the sensor hole.

Figure 7:
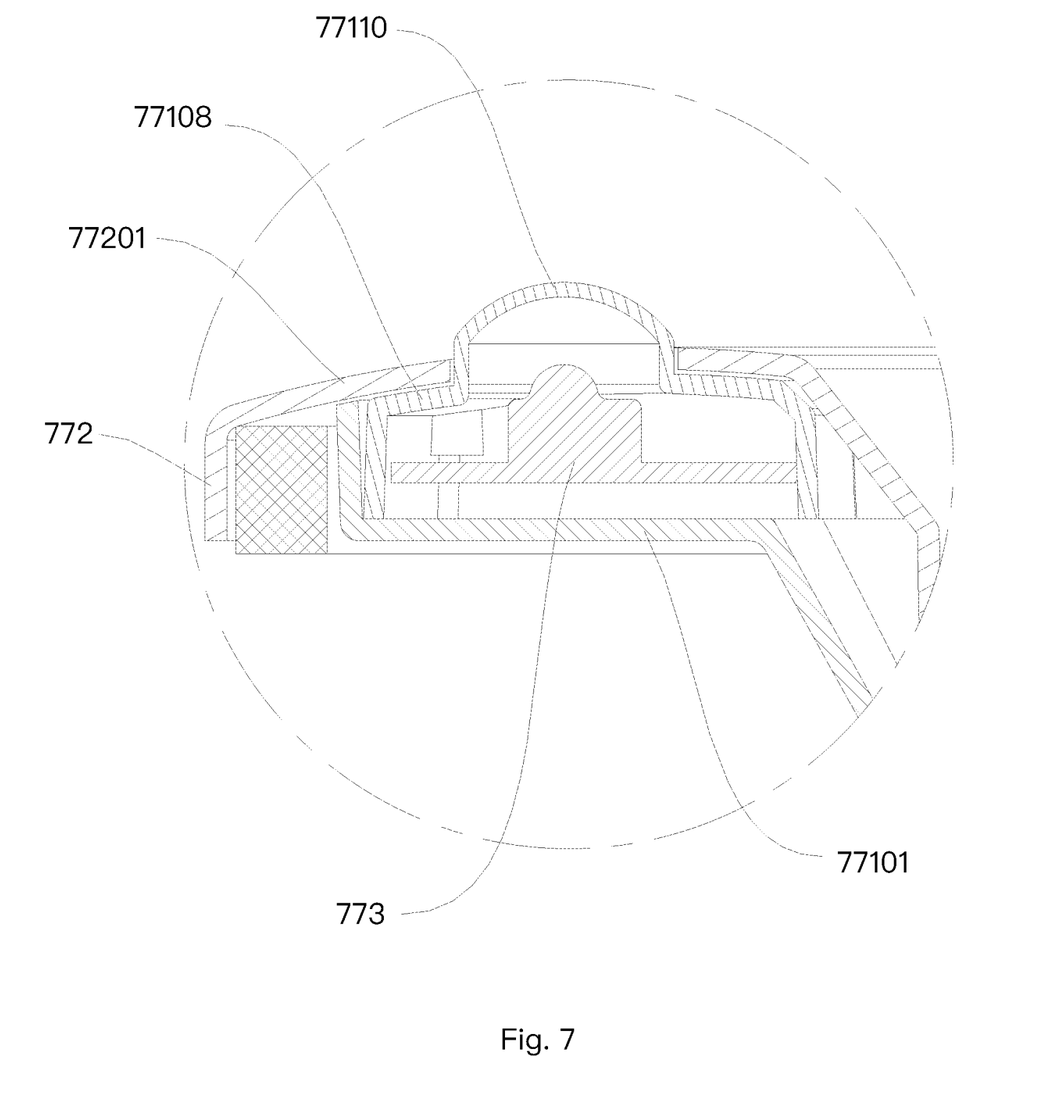
FIG. 7 illustrates a connection structure example.

For example, FIG. 7 shows a motion sensor 773 is placed in a motion detection grove 77101. There is a protective lens cover 77110 disposed above the motion sensor 773.

In FIG. 12, the lighting apparatus may also include a wireless sensor 802 for receiving an external command from a remote control. For example, a Bluetooth or an infrared sensor may be used for receiving an external command from a remote control, e.g. to turn on a sterilization process.

In some embodiments, the wireless sensor is integrated with the motion sensor and placed facing to the sensor hole.

In some embodiments, the base housing is a downlight housing with a pair of elastic units to attach to a cavity. For example, FIG. 12 and FIG. 13 show such an example.

Figure 15:
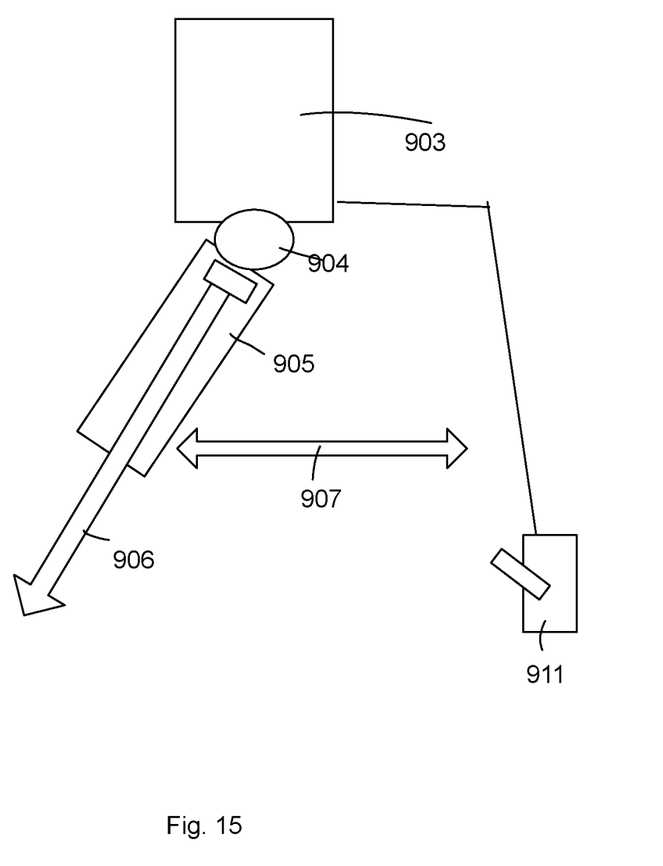
FIG. 15 illustrates a motor driven light example.

In FIG. 15, the first reflective cup 905 is moved by a motor 905 controlled by a driver 903 for changing a direction 907 of the first light 906 to scan a sterilization zone. In such case, the first light source may be integrated with the first reflective cup to form an movable ultra-violet light to scan different areas for sterilization.

In FIG. 15, the driver is electrically connected to a wall switch 911 mounted on a wall.

The driver 903 detects a predetermined on-off pattern of an operation to the wall switch 911 to determine activating the first light source to perform sterilization. For example, three on and off operation applied on the wall switch 911 within 3 seconds may be decoded as an instruction to start the sterilization process. The on-off pattern may also be configured to associate with different parameters, e.g. the time period of sterilization.

In some embodiments, the driver waits a waiting time period before turning on the first light source after the predetermined on-off pattern being detected. Such design gives a user sufficient to leave the room to be perform sterilization.

In some embodiments, when the sterilization is performed, the second light emits by the second light source is changed to a different light parameter. For example, in sterilization mode, the second light source emits a red light as a warning that the room is under sterilization.

In some embodiments, the second light source emits a different color of the second light during sterilization.

Figure 14:
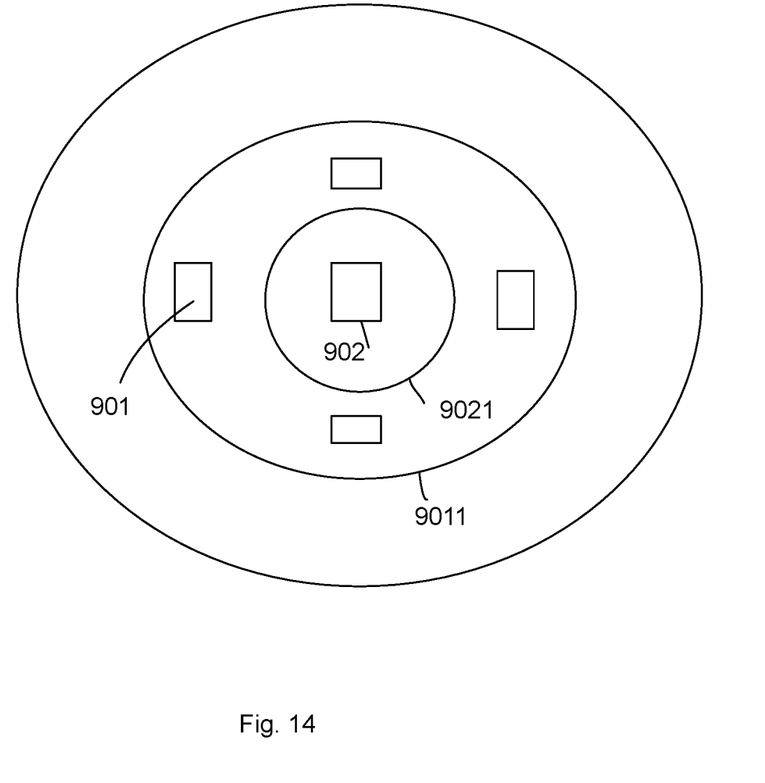
FIG. 14 illustrates another lighting apparatus example.

In FIG. 14, the first reflective cup 9011 surrounds the first reflective cup 9021.

The first scope is larger than the second scope. This is an opposite design compared with the previous example.

Please refer to FIG. 1 to FIG. 11, which illustrate another embodiments. The same reference among different drawings may refer to the same components and may not be repeated again for brevity.

Figure 1:
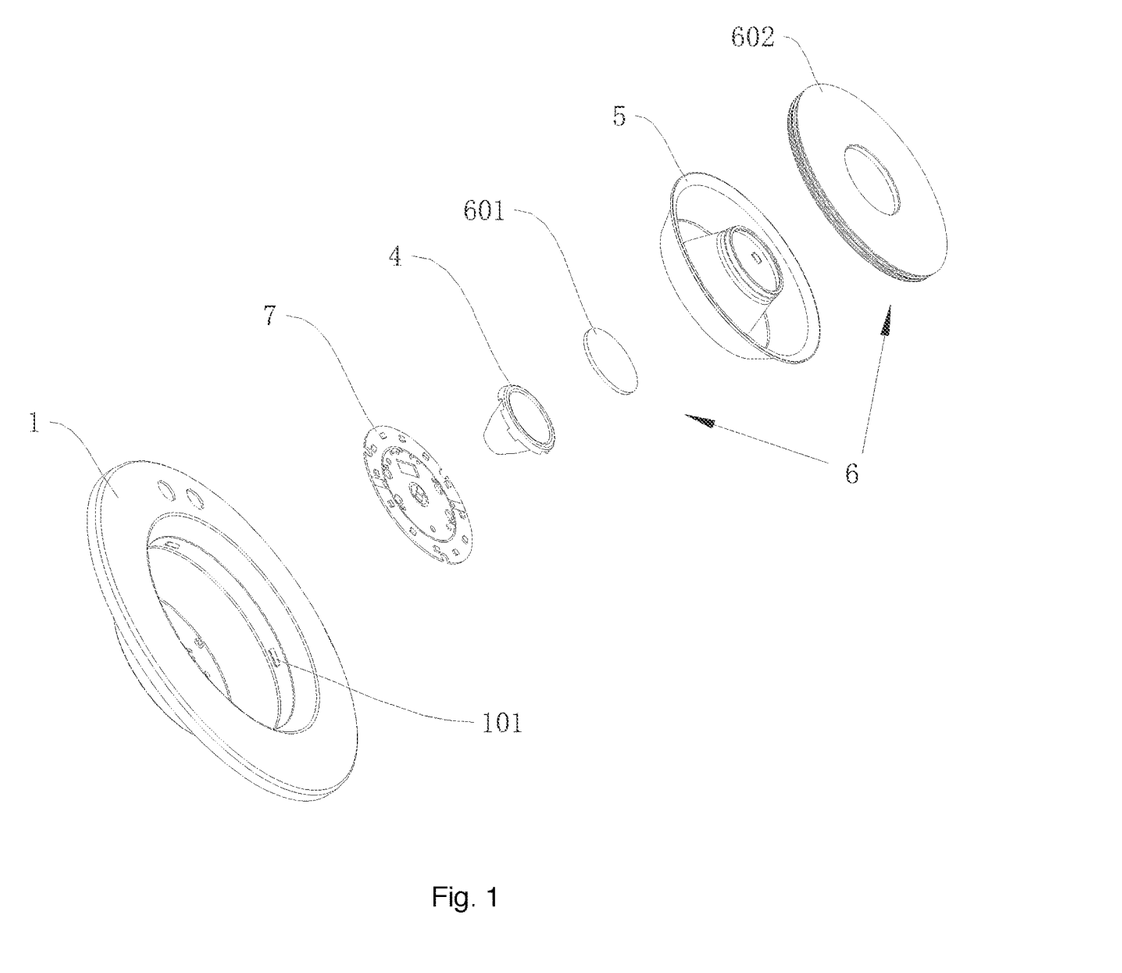
FIG. 1 illustrates an exploded view of a lighting apparatus embodiment.

In FIG. 1, a lighting apparatus includes a first light passing cover 601 and a second light passing cover 602 together forming a light passing cover 6. There is a second reflective cup 5 made of plastic material. There is a first reflective cup 4 inside the second reflective cup 5.

The first reflective cup 4 and the second reflective cup 5 are used for guiding a first light of a first light source and a second light of a second light source mounted on a light source plate 7.

The light source plate 7, the first reflective cup 4 and the second reflective cup 5 are disposed on the base housing 1. There is an aligning block 101 for aligning the light source plate 7 to be assembled to the base housing 1.

In FIG. 2, there is a first light source 2 surrounded by multiple second LED modules 3 of a second light source. The first light source 2 and the second light source are both placed on a light source plate 7.

Figure 3:
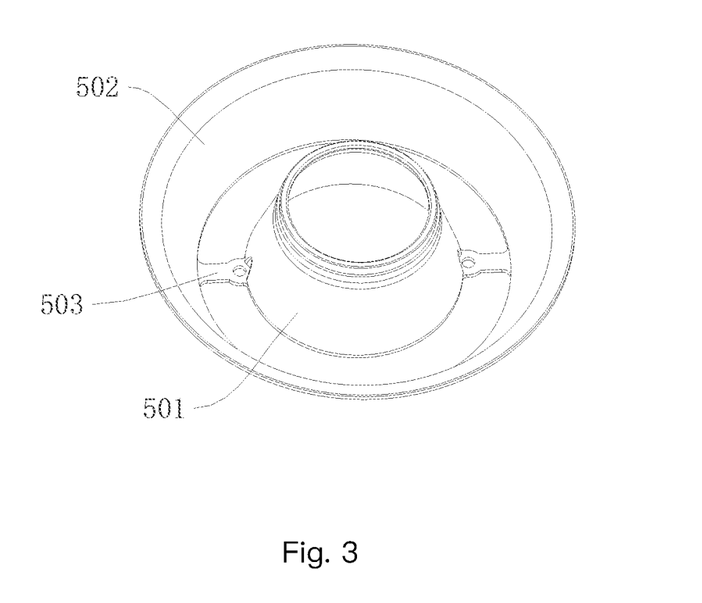
FIG. 3 illustrates a second reflective cup example.

In FIG. 3, the second reflective cup 5 has a reflective part 502, multiple bridge ribs 503 and an inner holder 501. The inner holder 501 and the reflective part 502 together guide the light of the second light source to desired directions.

Figure 4:
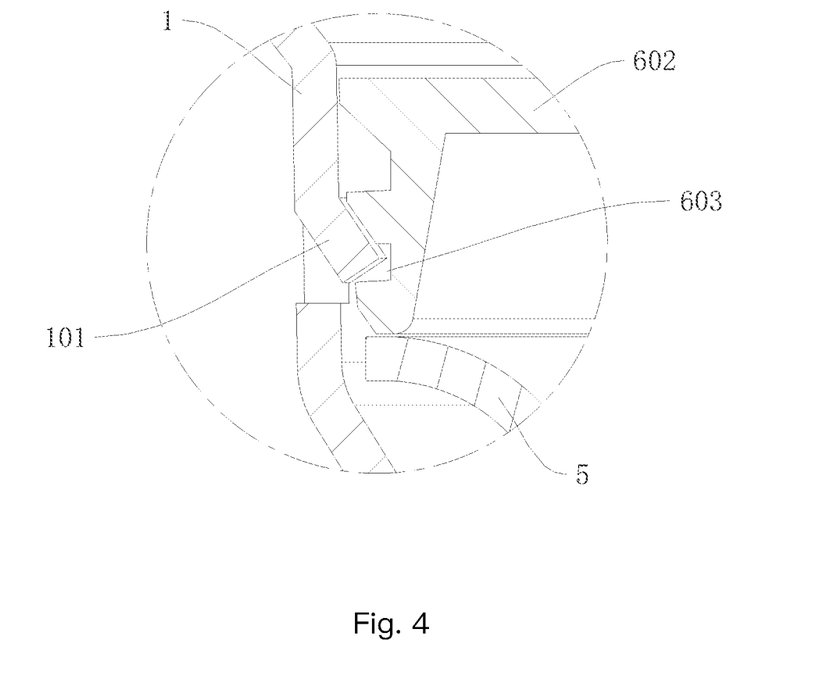
FIG. 4 illustrates a connection structure example.

In FIG. 4, the base housing has an aligning block 101 to be buckled to a light passing cover 602 and a ring buckle groove 603. The second reflective cup 5 is also buckled to the base housing 1.

Figure 5:
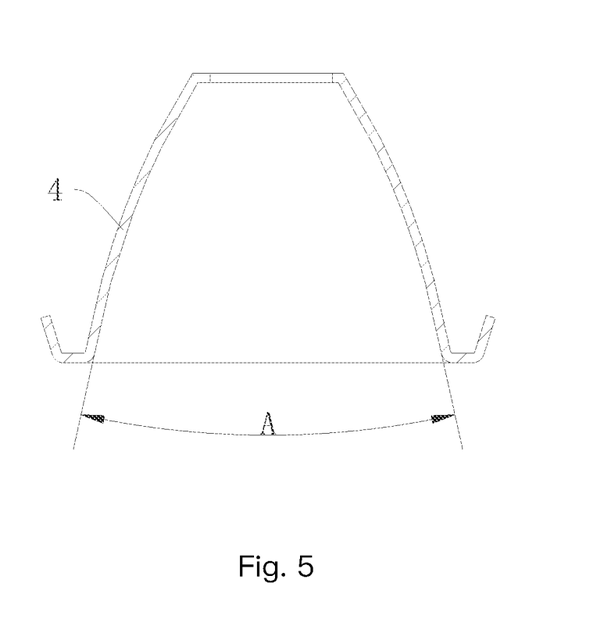
FIG. 5 illustrates a first reflective cup example.

In FIG. 5, the first reflective cup 5 is made of aluminum material. There is a scope A about 80 to 100 degrees spanning to perform sterilization.

Figure 6:
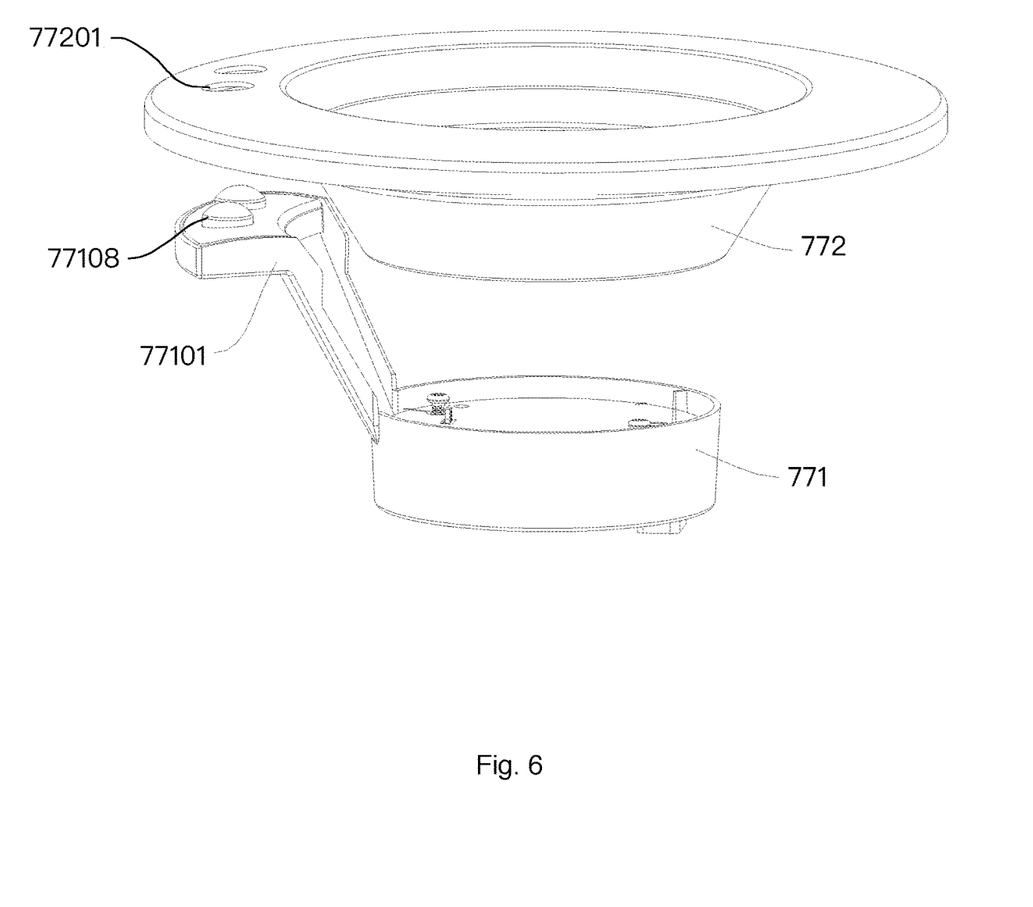
FIG. 6 illustrates a connection between a driver and a base housing.

In FIG. 6, the surface rim 772 has a sensor opening 77201 for inserting a motion sensor 77108 that is mounted on a holder 77101 extended from a driver box 771.

In FIG. 7, the motion sensor 773 is placed in a sensor groove 77101. There is a protective cover 77108 fixed by an edge of the sensor opening 77201 the surface rim 772.

In FIG. 8, the sensor 773 is placed on a stage 77104 held by an extending bar 77103 extended from a driver box 771 for holding a driver.

Figure 9:
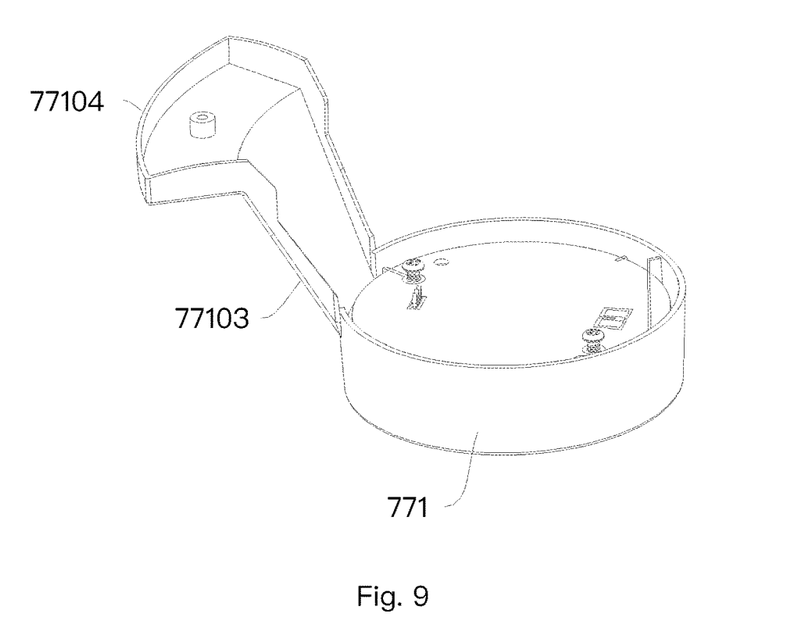
FIG. 9 illustrates a driver not mounted with the sensor module.

FIG. 9 shows a status that the sensor 773 is not placed yet.

Figure 10:
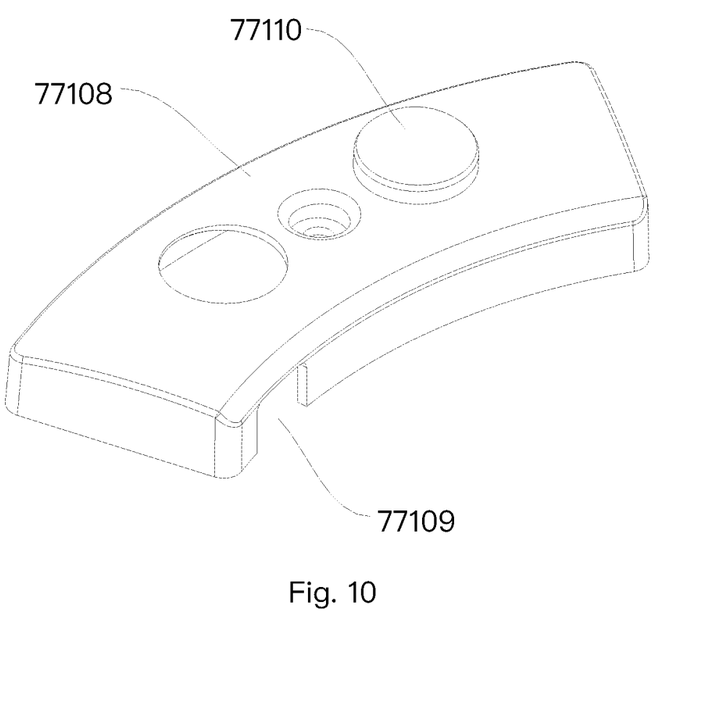
FIG. 10 illustrates a sensor hole and a sensor lens.

FIG. 10 shows a sensor 77110 placed on a sensor plate 77108 leaving a groove opening 77109 for passing a wire.

Figure 11:
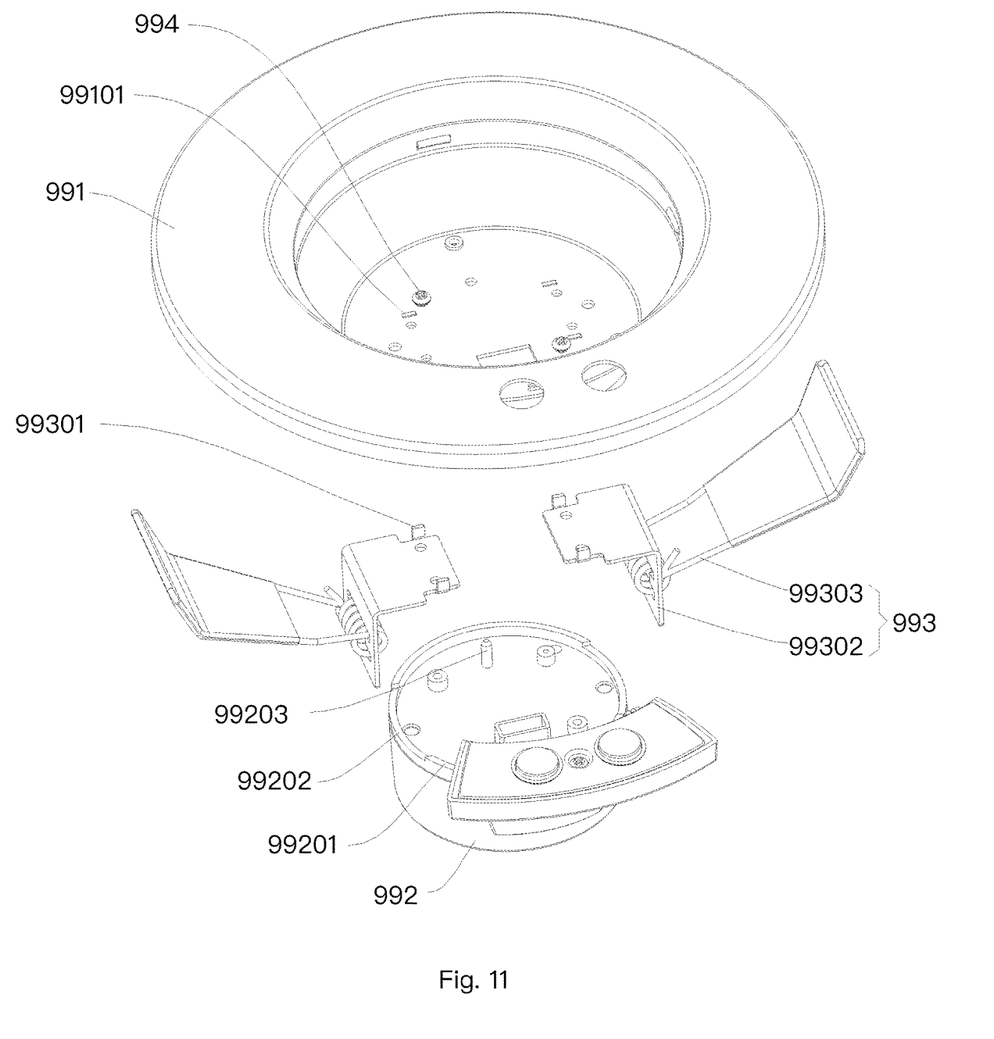
FIG. 11 illustrates an exploded view of another embodiment.

FIG. 11 shows a pair of elastic units 993 with an extending arm 99303 and a spring 99302. There is a protruding pin 9301 to be inserted to a corresponding hole 99101 of a base housing 991. There is a screw 994 to attaching the driver box 992. The driver box has an extending sensor bar 99201 to hold one or more sensors. In addition, the driver box 992 has an aligning column 99203 and a protruding wall 99202 for attaching to other components.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings.

The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

The invention claimed is:

1. A lighting apparatus, comprising:
a first light source for emitting a first light;
a second light source for emitting a second light;
a first reflective cup for limiting the first light in a first scope;
a second reflective cup for limiting the second light in a second scope;
a base housing for disposing the first reflective cup and the second reflective cup;
a driver for selectively providing a first driving current to the first light source and a second driving current to the second light source, wherein the first light is an ultraviolet light; and
a motion sensor, wherein the driver turns off the first driving current when the motion sensor indicates an object approaching the first scope.

2. The lighting apparatus of claim 1, wherein the first reflective cup is surrounded by the second reflective cup.

3. The lighting apparatus of claim 2, wherein the second light source comprises multiple second LED modules, wherein the first light source and the multiple second LED modules are disposed on a same circuit board, wherein the multiple second LED modules surround the first light source.

4. The lighting apparatus of claim 1, wherein the first reflective cup comprises aluminum material.

5. The lighting apparatus of claim 4, wherein the second reflective cup is made of plastic material.

6. The lighting apparatus of claim 1, further comprising a first light passing cover and a second light passing cover, wherein the second light passing cover has a cover opening for fixing the first light passing cover, wherein the first light passes through the first light passing cover, wherein the second light passes through the second light passing cover.

7. The lighting apparatus of claim 6, wherein first light passing cover is made of silica glass material.

8. The lighting apparatus of claim 1, wherein the base housing comprises a surface rim for concealing a cavity for installing the lighting apparatus, wherein the surface rim has a sensor hole for the motion sensor to detect the object.

9. The lighting apparatus of claim 8, wherein the motion sensor is integrated with the driver, wherein the motion sensor is placed to a motion detection groove of the surface rim for facing to the sensor hole.

10. The lighting apparatus of claim 8, further comprising a wireless sensor for receiving an external command from a remote control.

11. The lighting apparatus of claim 10, wherein the wireless sensor is integrated with the motion sensor and placed facing to the sensor hole.

12. The lighting apparatus of claim 1, wherein the base housing is a downlight housing with a pair of elastic units to attach to a cavity.

13. The lighting apparatus of claim 1, wherein the first reflective cup is moved by a motor for changing a direction of the first light to scan a sterilization zone.

14. The lighting apparatus of claim 1, wherein the driver is electrically connected to a wall switch mounted on a wall, wherein the driver detects a predetermined on-off pattern of an operation to the wall switch to determine activating the first light source to perform sterilization.

15. The lighting apparatus of claim 14, wherein the driver waits a waiting time period before turning on the first light source after the predetermined on-off pattern being detected.

16. The lighting apparatus of claim 15, wherein when the sterilization is performed, the second light emits by the second light source is changed to a different light parameter.

17. The lighting apparatus of claim 16, wherein the second light source emits a different color of the second light during sterilization.

18. The lighting apparatus of claim 1, wherein the first reflective cup surrounds the first reflective cup, wherein the first scope is larger than the second scope.

* * * * *